United States Patent
Fotouhi et al.

(10) Patent No.: US 11,149,318 B2
(45) Date of Patent: Oct. 19, 2021

(54) METHODS AND DEVICES FOR DETECTION OF PATHOGENS

(71) Applicant: Graphene-DX, Inc., Boston, MA (US)

(72) Inventors: Mohammed Fotouhi, Weston, MA (US); Mohammad E. Taslim, Needham, MA (US); Mehdi Abedi, Brighton, MA (US); Edward Alvin Greenfield, Stoughton, MA (US); Reza Mollaaghababa, Natick, MA (US); Namal Nawana, Weston, MA (US)

(73) Assignee: GRAPHENE-DX, INC., Boston, MA (US)

( * ) Notice: Subject to any disclaimer, the term of this patent is extended or adjusted under 35 U.S.C. 154(b) by 106 days.

(21) Appl. No.: 16/260,773

(22) Filed: Jan. 29, 2019

(65) Prior Publication Data
US 2019/0284615 A1 Sep. 19, 2019

Related U.S. Application Data

(60) Provisional application No. 62/703,702, filed on Jul. 26, 2018, provisional application No. 62/676,079, (Continued)

(51) Int. Cl.
*C12Q 1/689* (2018.01)
*G01N 33/569* (2006.01)
(Continued)

(52) U.S. Cl.
CPC ............... *C12Q 1/689* (2013.01); *C12Q 1/04* (2013.01); *G01N 33/5438* (2013.01);
(Continued)

(58) Field of Classification Search
CPC . C12Q 1/689; C12Q 1/04; C12Q 1/24; G01N 33/5438; G01N 33/56911;
(Continued)

(56) References Cited

U.S. PATENT DOCUMENTS

| | | |
|---|---|---|
| 4,983,102 A | 1/1991 | Swain |
| 6,037,168 A | 3/2000 | Brown |

(Continued)

FOREIGN PATENT DOCUMENTS

| | | |
|---|---|---|
| CA | 2971589 A1 | 6/2016 |
| DE | 19600521 A1 | 7/1996 |

(Continued)

OTHER PUBLICATIONS

Pandey, Ashish, et al. "Graphene-interfaced electrical biosensor for label-free and sensitive detection of foodborne pathogenic E. coli O157: H7." Biosensors and Bioelectronics 91, Dec. 16, 2016: 225-231. (Year: 2016).*

(Continued)

*Primary Examiner* — Robert J Eom
(74) *Attorney, Agent, or Firm* — Morgan, Lewis & Bockius LLP

(57) ABSTRACT

In one aspect, a method of detecting a pathogen, e.g., *listeria* bacterium, *chlamydia* bacteria, gonorrhea bacteria and/or HPV, in a sample is disclosed, which comprises bringing a sample into contact with a graphene layer functionalized with an antibody exhibiting specific binding to the pathogen, monitoring electrical resistance of said antibody-functionalized graphene layer in response to interaction with said sample, and detecting presence of the pathogen in said sample by detecting a change in said electrical resistance indicative of interaction of the pathogen with said antibody-functionalized graphene layer. For example, a decrease of the electrical resistance of the graphene layer can indicate the presence of the pathogen in the sample under study. In some embodiments, a method according to the present teachings is capable of detecting pathogens, such as *listeria* bacteria, *chlamydia* bacteria, gonorrhea bacteria and HPV in (Continued)

a sample at a concentration as low as 4 cfu per 100 grams of a sample.

18 Claims, 12 Drawing Sheets

Related U.S. Application Data filed on May 24, 2018, provisional application No. 62/623,038, filed on Jan. 29, 2018.

(51) Int. Cl.
   C12Q 1/04     (2006.01)
   G01N 33/543   (2006.01)
   C12Q 1/24     (2006.01)
   G01N 33/571   (2006.01)

(52) U.S. Cl.
   CPC . *G01N 33/56911* (2013.01); *G01N 33/56927* (2013.01); *C12Q 1/24* (2013.01); *G01N 33/571* (2013.01); *G01N 2333/025* (2013.01); *G01N 2333/22* (2013.01)

(58) Field of Classification Search
   CPC ........... G01N 33/56927; G01N 33/571; G01N 2333/025; G01N 2333/22
   See application file for complete search history.

(56) References Cited

U.S. PATENT DOCUMENTS

| | | | |
|---|---|---|---|
| 8,575,663 | B2 | 11/2013 | Lieber et al. |
| 8,695,810 | B2 | 4/2014 | Gao |
| 8,907,384 | B2 | 12/2014 | Pace et al. |
| 9,146,209 | B2 | 9/2015 | Johnson et al. |
| 9,160,024 | B1 | 10/2015 | Moore et al. |
| 9,162,885 | B2 | 10/2015 | Lee et al. |
| 9,612,240 | B2 | 4/2017 | Johnson, Jr. et al. |
| 9,618,476 | B2 | 4/2017 | Goldsmith |
| 9,664,674 | B2 | 5/2017 | Taslim et al. |
| 9,735,366 | B2 | 8/2017 | Turchanin |
| 9,765,395 | B2 | 9/2017 | Goldsmith |
| 9,857,328 | B2 | 1/2018 | Hoffman |
| 9,859,394 | B2 | 1/2018 | Hoffman et al. |
| 9,887,352 | B2 | 2/2018 | Bessonov et al. |
| 10,168,297 | B2 | 1/2019 | Johnson, Jr. et al. |
| 10,401,352 | B2 | 9/2019 | Taslim et al. |
| 10,429,342 | B2 | 10/2019 | Hoffman et al. |
| 10,429,381 | B2 | 10/2019 | Hoffman |
| 10,607,989 | B2 | 3/2020 | Hoffman |
| 10,660,697 | B2 | 5/2020 | Xiao et al. |
| 10,751,986 | B2 | 8/2020 | Lerner et al. |
| 10,758,303 | B2 | 9/2020 | Xiao et al. |
| 10,782,285 | B2 | 9/2020 | Taslim et al. |
| 10,811,539 | B2 | 10/2020 | van Rooyen et al. |
| 10,968,481 | B2 | 4/2021 | van Rooyen et al. |
| 2004/0146863 | A1 | 7/2004 | Pisharody et al. |
| 2005/0072213 | A1 | 4/2005 | Besnard et al. |
| 2008/0017737 | A1 | 1/2008 | So et al. |
| 2009/0092965 | A1 | 4/2009 | Weiss et al. |
| 2009/0311727 | A1 | 12/2009 | Watkins et al. |
| 2010/0222224 | A1 | 9/2010 | Suni et al. |
| 2012/0129198 | A1 | 5/2012 | Buechler et al. |
| 2012/0156688 | A1 | 6/2012 | McAlpine et al. |
| 2012/0264232 | A1 | 10/2012 | Kramer et al. |
| 2013/0164859 | A1 | 6/2013 | Johnson et al. |
| 2013/0217598 | A1 | 8/2013 | Ludwig et al. |
| 2014/0220617 | A1 | 8/2014 | Yung et al. |
| 2014/0295406 | A1 | 10/2014 | Sundvor et al. |
| 2015/0011020 | A1 | 1/2015 | Sundvor et al. |
| 2015/0065363 | A1 | 3/2015 | Johnson, Jr. et al. |
| 2015/0173883 | A1 | 6/2015 | Ingber et al. |
| 2015/0307936 | A1 | 10/2015 | Goldsmith |
| 2015/0309018 | A1 | 10/2015 | Goldsmith |
| 2015/0346141 | A1 | 12/2015 | Johnson et al. |
| 2016/0025675 | A1 | 1/2016 | Goldsmith |
| 2016/0054312 | A1 | 2/2016 | Goldsmith |
| 2016/0097764 | A1 | 4/2016 | Taslim et al. |
| 2016/0223538 | A1 | 8/2016 | McAlpine et al. |
| 2017/0067888 | A1 | 3/2017 | Taslim et al. |
| 2017/0212116 | A1* | 7/2017 | Braga .............. G01N 33/56983 |
| 2017/0299602 | A1 | 10/2017 | Johnson, Jr. et al. |
| 2017/0307562 | A1 | 10/2017 | Goldsmith |
| 2017/0361599 | A1 | 12/2017 | Lerner et al. |
| 2017/0365474 | A1 | 12/2017 | Pan et al. |
| 2017/0365477 | A1 | 12/2017 | Pan et al. |
| 2017/0365562 | A1 | 12/2017 | Pan et al. |
| 2018/0037952 | A1 | 2/2018 | Goldsmith |
| 2019/0079068 | A1 | 3/2019 | Taslim et al. |
| 2019/0187090 | A1 | 6/2019 | Grabbert et al. |
| 2019/0284615 | A1 | 9/2019 | Fotouhi et al. |
| 2019/0317081 | A1 | 10/2019 | Taslim et al. |
| 2020/0011860 | A1 | 1/2020 | Nawana et al. |
| 2020/0141931 | A1 | 5/2020 | Hoffman |
| 2020/0300845 | A1 | 9/2020 | Fotouhi et al. |
| 2021/0102937 | A1 | 4/2021 | Taslim et al. |

FOREIGN PATENT DOCUMENTS

| | | |
|---|---|---|
| EP | 3308153 A1 | 4/2018 |
| EP | 3344980 A1 | 7/2018 |
| EP | 3491370 A1 | 6/2019 |
| EP | 3201627 B1 | 2/2020 |
| EP | 3149464 B1 | 9/2020 |
| EP | 3280822 B1 | 11/2020 |
| WO | 2001/47704 A1 | 7/2001 |
| WO | 2014/160861 A1 | 10/2014 |
| WO | 2017/103269 A1 | 6/2017 |
| WO | 2017/194746 A1 | 11/2017 |
| WO | 2018/200794 A1 | 11/2018 |

OTHER PUBLICATIONS

Zuo, Peng, et al. "A PDMS/paper/glass hybrid microfluidic biochip integrated with aptamer-functionalized graphene oxide nano-biosensors for one-step multiplexed pathogen detection." Lab on a Chip 13.19 (2013): 3921-3928. (Year: 2013).*
Jai, Fei, et al. "Impedimetric *Salmonella aptasensor* using a glassy carbon electrode modified with an electrodeposited composite consisting of reduced graphene oxide and carbon nanotubes." Microchimica Acta 183.1: 337-344. (Year: 2015).
[No Author Listed] Agilent Technologies International sarl, Agilent B1500A Semiconductor Device Analyzer User's Guide, Edition 6, Nov. 2007, p. 1-588.
[No Author Listed] Agilent Technologies, "Agilent B1500A Semiconductor Device Analyzer User's Guide", Edition 7, Oct. 2008, p. 1-628.
Asad, M., et al., "Surface Acoustic Wave Based H2S Gas Sensors Incorporating Sensitive Layers of Single Wall Carbon Nanotubes Decorated With Cunanoparticles," Sensors and Actuators B 198 (2014) pp. 134-141.
Balasubramanian, K, et al., "Chemically Functionalized Carbon Nanotubes," Small (2005) vol. 1, No. 2, pp. 180-192.
Bard, A., et al., "Electrochemical Methods, Fundamentals and Applications," Second Edition, John Wiley & Sons, Inc., New York, Copyright (2001) © John Wiley & Sons, Inc. All rights reserved. ISBN 0-471-04372-9, pp. 1-850.
Bhattacharya, M., et al., "Carbon Nanotube Based Sensors for the Detection of Viruses," Sensors and Actuators B 155, (2011), pp. 67-74.
Bianco, A., Presentation Nanotube Functionalization and Therapeutic Applications, Immunologie et Chimie Therapeutiques, CNRS, Strasbourg, France, Nanosoft (Roscoff), May 21-25, 2007, pp. 1-68.
Bietz, J.A., et al., "Identity of High Molecular Weight Gliadin and Ethanol-Soluble Glutenin , Subunits of Wheat: Relation to Gluten Structure," Cereal Chern. (1980), vol. 57, No. 6, pp. 415-421.
Capparelli, R., et al., "Quantification of Gliadin Levels to the Picogram Level by Flow Cytometry," Wiley-Liss, Inc., Cytometry Part A 63A, (2005), pp. 108-113.

(56) References Cited

OTHER PUBLICATIONS

Chakravarty, P., et al., "Thermal Ablation of Tumor Cells With Antibody-Functionalized Single-Walled Carbon Nanotubes," PNAS, Jun. 24, 2008, vol. 105, No. 25, pp. 8697-8702.

Chopra, S., et al., "Selective Gas Detection Using a Carbon Nanotube Sensor," Applied Physics Letters, vol. 83, No. 11, Sep. 15, 2003, pp. 2280-2282.

Coyle, B., et al., "Carbon-Binding Designer Proteins That Discriminate Between sp2-and sp3-Hybridized Carbon Surfaces," American Chemical Society, Langmuir, (2013), vol. 29, pp. 4839-4846.

De Gracia Villa, M., et al., "Carbon Nanotube Composite Peptide-Based Biosensors As Putative Diagnostic Tools for Rheumatoid Arthritis," Biosensors and Bioelectronics, (2011), vol. 27 pp. 113-118.

De Leo, F., et al., "Structural and Dynamic Properties of Monoclonal Antibodies Immobilized on CNTs: A Computational Study," Chemistry European Journal, (2013), vol. 19, pp. 12281-12293.

Deng, C., et al., "Electrochemical Detection of Nitrite Based on the Polythionine/Carbon Nanotube Modified Electrode," Thin Solid Films 520, (2012), pp. 7026-7029.

Desai, S.C., et al., "Hypergolic Fuel Detection Using Individual Single Walled Carbon Nanotube Networks," Journal of Applied Physics, (2010) vol. 107, pp. 114509-1-114509-17.

Didar, T.F., et al., Improved treatment of systemic blood infections using antibiotics with extracorporeal opsonin hemoadsorption. Biomaterials. Oct. 2015;67:382-92. doi: 10.1016/j.biomaterials.2015.07.046. Epub Jul. 26, 2015.

Drouvalakis, K., et al., Peptide-Coated Nanotube-Based Biosensor for the Detection of Disease-Specific Autoantibodies in Human Serum, Biosensors and Bioelectronics, (2008), vol. 23, pp. 1413-1421.

Efrat, A., et al., Curve Matching, Time Warping, and Light Fields: New Algorithms for Computing Similarity Between Curves, Department of Computer Science, University of Arizona, Suresh Venkatasubramanian, At&T Labs—Research, (2007), pp. 1-19.

Eissa, S., et al., "A Graphene-Based Electrochemical Competitive Immunosensor for the Sensitive Detection of Okadaic Acid in Shellfish", Nanoscale, (2012), vol. 4, pp. 7593-7599.

Extended European Search Report for Application No. 15846637.5, dated Apr. 3, 2018 (7 pages).

Fadel, T., et al., "Clustering of Stimuli on Single-Walled Carbon Nanotube Bundles Enhances Cellular Activation," Langmuir, (2010), vol. 26 No. 8, pp. 5645-5654.

Fernstrom, J.D., et al., "Mechanisms for Sweetness1-3," The Journal of Nutrition, Supplement May 9, 2012, pp. 1S of 8S.0.

Forsyth, R., et al., Graphene Field Effect Transistors for Biomedical Applications: Current Status and Future Prospects. Diagnostics (Basel). Jul. 26, 2017;7(3), 18 pages. pii: E45. doi: 10.3390/diagnostics7030045.

Fu, B.X., "Salt-Induced Disaggregation/Solubilization of Gliadin and Glutenin Proteins in Water," Journal of Cereal Science 24 (1996) 241-246.

Gao, N., et al., Specific detection of biomolecules in physiological solutions using graphene transistor biosensors. Proc Natl Acad Sci U S A. Dec. 20, 2016;113(51)14633-14638. doi: 10.1073/pnas.1625010114. Epub Dec. 5, 2016.

Garcia-Aljaro, C., et al., "Carbon Nanotubes-Based Chemiresistive Biosensors for Detection of Microorganisms," Biosensors and Bioelectronics 26 (2010) 1437-1441.

Gowda, P., et al., Chemical Vapor Detection Using Nonlinear Electrical Properties of Carbon Nanotube Bundles, Nanotechnology vol. 25 (2014) pp. 1-5.

Greene, F., "In Vitro Synthesis of Wheat (*Triticum aestivum* L.) Storage Proteins1," Plant Physiol. (1981) vol. 68, pp. 778-783.

Heller, D., et al., "Peptide Secondary Structure Modulates Single-Walled Carbon Nanotube Fluorescence as a Chaperone Sensor for Nitroaromatics," PNAS May 24, 2011, vol. 108, No. 21, pp. 8544-8549.

Hnaien, M., et al., "Impedimetric Microbial Biosensor Based on Single Wall Carbon Nanotube Modified Microelectrodes for Trichloroethylene Detection," Electrochimica Acta 56 (2011) pp. 10353-10358.

Hoaglan, R., "The Determination of Gliadin or Alcohol-Soluble Protein in Wheat Flour," The Journal of Industrial and Engineering Chemistry, (1911), Proteins of the Wheat Kernel Pub by Carnegie Inst, pp. 838-842.

Huang, T.S. et al., "Immobilization of Antibodies and Bacterial Binding on Nanodiamond and Carbon Nanotubes for Biosensor Applications," Diamond and Related Materials vol. 13, (2004), pp. 1098-1102.

Huang, Y., et al., "Graphene-Based Biosensors for Detection of Bacteria and Their Metabolic Activities", Journal of Materials Chemistry, (2011) vol. 21, pp. 12358-12362.

Hui, Y., et al., "A 2.8 Ghz Combined Mode of Vibration Aluminum Nitride MEMS Resonator With High Figure of Merit Exceeding 45," (2013) Joint UFFC, EFTF and PFM Symposium pp. 930-932.

Hui, Y., et al., "Resonant Infrared Detector Based on a Piezoelectric Fishnet Metasurface," (2015) IEEE, pp. 1-3.

Huntington, M.D., et al., A Portable, Benchtop Photolithography System Based,"On a Solid-State Light Source," Supporting Information, Small, (2011), pp. S1-S7.

Huntington, M.D., et al., A Portable, Benchtop Photolithography System Based,"On a Solid-State Light Source," Small (2011), vol. 7, No. 22, pp. 3144-3147.

International Search Report and Written Opinion for Application No. PCT/US2015/053793, dated Jan. 4, 2016 (12 Pages).

International Search Report and Written Opinion for Application No. PCT/US2019/15579, dated Jun. 18, 2019 (13 pages).

International Search Report and Written Opinion for Application No. PCT/US2019/34043, dated Sep. 30, 2019 (12 Pages).

International Preliminary Report on Patentability for Application No. PCT/US2015/053793, dated Apr. 13, 2017 (11 Pages).

Jain, S., et al., "Development of an Antibody Functionalized Carbon Nanotube Biosensor for Foodborne Bacterial Pathogens," J Biosens Bioelectron (2012), S:11, pp. 1-7.

Jiang, P., et al., "Molecular Mechanisms of Sweet Receptor Function," Chem. Senses 30 (Suppl 1): (2005), pp. 117-118.

Jin, X., et al., "Detection of Human Adenovirus Hexon Antigen Using Carbon Nanotube Sensors," Journal of Virological Methods vol. 171, (2011), pp. 405-407.

Kabbe, G., Presentation "Functionalization: Tailoring Nanocarbons Through Attached Molecules and Particles," Freie Universitat Berlin, (2011).

Kang, J.H., et al., An extracorporeal blood-cleansing device for sepsis therapy. Nat Med. Oct. 2014;20(10):1211-6. doi: 10.1038/nm.3640. Epub Sep. 14, 2014.

Ke, G., et al., "A Novel Strategy to Functionalize Carbon Nanotubes With Cellulose Acetate Using Triazines As Intermediated Functional Groups," Carbohydrate Polymers 79 (2010), pp. 775-782.

Kim, B., et al., "Family-Selective Detection of Antibiotics Using Antibody-Functionalized Carbon Nanotube Sensors," Sensors and Actuators B 166-167 (2012) pp. 193-199.

Kim, K., et al., Presentation "Antibody-Functionalized Carbon Nanotubes in Cancer Therapy," Apr. 28, 2008, pp. 1-72.

Kodali, V.K., et al., "Nonperturbative Chemical Modification of Graphene for Protein Micropatterning," Langmuir (2011), vol. 27, No. (3), pp. 863-865.

Kruss, S., et al., "Neurotransmitter Detection Using Corona Phase Molecular Recognition on Fluorescent Single-Walled Carbon Nanotube Sensors," American Chemical Society J. Am. Chem. Soc. (2014), vol. 136, pp. 713-724.

Kuzmany, H., et al., "Functionalization of Carbon Nanotubes," Synthetic Metals vol. 141, (2004), pp. 113-122.

Lee, P.P., et al., "Targeting Colorectal Cancer Cells With Single-Walled Carbon Nanotubes Conjugated to Anticancer Agent SN-38 and EGFR Antibody," Biomaterials vol. 34, (2013) pp. 8756-8765.

Lerner, M.B., et al., Presentation Detecting Lyme Disease Using Antibody-Functionalized Single-Walled Carbon Nanotube Transistors, Department of Physics and Astronomy, University of Pennsylvania, 209 South 33rd Street, Philadelphia, PA 19104, (2014).

(56) References Cited

OTHER PUBLICATIONS

Li, C., et al., Mass Detection Using Carbon Nanotube-Based Nanomechanical Resonators, Applied Physics Letters vol. 84, No. 25, Jun. 21, 2004, pp. 5246-5248.
Li, R., et al., P-Glycoprotein Antibody Functionalized Carbon Nanotube Overcomes the Multidrug Resistance of Human Leukemia Cells, ACSNANO (2010), vol. 4, No. 3, pp. 1399-1408.
Liang, X., et al., "Toward Clean and Crackless Transfer of Graphene," ACSNANO, (2011), vol. 5, No. 11, pp. 144-9153.
Lillehoj, P.B., et al., Rapid electrochemical detection on a mobile phone. Lab Chip. Aug. 7, 2013;13(15):2950-5. doi: 10.1039/c3lc50306b.
Liu, J., et al., "Visible Light Detection Using Single-Walled Carbon Nanotube Film and Gold Nanoparticles or Nanorods," Journal of Applied Physics, vol. 107, (2010), pp. 1-4.
Ma, P., et al., "Dispersion and Functionalization of Carbon Nanotubes for Polymer-Based Nanocomposites: A Review," Composites: Part A 41 (2010), pp. 1345-1367.
Mairal, T., et al, "Microfluorimeter with disposable polymer chip for detection of coeliac disease toxic gliadin," Lab on a Chip, vol. 9, No. 24, Jan. 1, 2009, pp. 3535-3542.
Mao, S., et al., "Specific Biosensing Using Carbon Nanotubes Functionalized With Gold Nanoparticle—Antibody Conjugates" Carbon, vol. 48 (2010), pp. 479-486.
Mao, S., et al., Graphene-based electronic biosensors. J Mater Res, 2017;32(15):2954-2965.
Marches, R., et al., "Specific Thermal Ablation of Tumor Cells Using Single-Walled Carbon Nanotubes Targeted by Covalently-Coupled Monoclonal Antibodies," Int. J. Cancer: (2009), vol. 125, pp. 2970-2977.
Margolskee, RF., "Molecular Mechanisms of Bitter and Sweet Taste Transduction," The Journal of Biological Chemistry, (Issue of Jan. 4, 2002), vol. 277, No. 1, pp. 1-4.
Maruyama, H., et al., "Evaluation of Thermal Conductivity of Single Carbon Nanotubes in Air and Liquid Using a Fluorescence Temperature Sensor," Applied Physics Letters, 103, (2013), pp. 1-5.
Matsumoto, K. (Ed.), "Frontiers of Graphene and Carbon Nanotubes, Devices and Application," Springer Japan KK Is Part of Springer Science+Business Media (2015), (www.springercom).
McDevitt, MR,, et al., "Tumor Targeting With Antibody-Functionalized, Radiolabeled Carbon Nanotubes," The Journal of Nuclear Medicine, (2007), vol. 48, No. 7, pp. 1180-1189.
Menard-Moyon, C., et al., "Functionalized Carbon Nanotubes for Probing and Modulating Molecular Functions," Chemistry & Biology 17, Feb. 26, 2010, pp. 107-115.
Miller, K. et al. "Portable gluten biosensor (Thesis)," University of Arizona, May 31, 2009; pp. FP-45, retrieved Mar. 13, 2018 from <http://hdl.handle.net/10150/192520>.
Moreira, F., et al., "Artificial Antibodies for Troponin T by its Imprinting on the Surface of Multiwalled Carbon Nanotubes: Its Use As Sensory Surfaces," Biosensors and Bioelectronics, vol. 28 (2011) pp. 243-250.
Moreno, M., Analysis of Polyphenols in White Wine by CZE With Amperometric Detection Using Carbon Nanotube-Modified Electrodes, Electrophoresis, (2011), vol. 32, pp. 877-883.
Moron, B., et al., "Sensitive Detection of Cereal Fractions That Are Toxic to Celiac Disease Patients by Using Monoclonal Antibodies to a Main Immunogenic Wheat Peptide1-3," Am J Clin Nutr, (2008), vol. 87 pp. 405-414.
Mulvey. J.J., et al., "Self-Assembly of Carbon Nanotubes and Antibodies on Tumours for Targeted Amplified Delivery," Nature Nanotechnology, (2013), vol. 8, pp. 763-771.
Naguib, N., et al., "Effect of Carbon Nanofibre Structure on the Binding of Antibodies," Nanotechnology, vol. 16, (2005), pp. 567-571.
Nassef, H.M., et al., Electrochemical immunosensor for detection of celiac disease toxic gliadin in foodstuff. Anal Chem. Dec. 1, 2008;80(23):9265-71. doi: 10.1021/ac801620j.
Neves, M.M., et al., An electrochemical deamidated gliadin antibody immunosensor for celiac disease clinical diagnosis. Analyst. Apr. 7, 2013;138(7):1956-8. doi: 10.1039/c3an36728b. Epub Feb. 12, 2013.
Neves, Marta MPS, et al. "Voltammetric immunosensor for the diagnosis of celiac disease based on the quantification of anti-gliadinantibodies." Sensors and Actuators B: Chemical 163.1 (2012): 253-259.
Orth, RA., et al., "A Comparative Study of the Proteins of Wheats of Diverse Baking Qualities," American Association of Cereal Chemists, Inc., (1972), pp. 268-275.
Pei-Tzu, C., et al, "Detection of Gliadin in Foods Using a Quartz Crystal Microbalance Biosensor That Incorporates Gold Nanoparticles," Journal of Agricultural and Food Chemistry, v. 60, No. 26, Jul. 4, 2012, pp. 6483-6492.
Penza, M., et al., Carbon Nanotube Acoustic and Optical Sensors for Volatile Organic Compound Detection, Nanotechnology, (2005), vol. 16, pp. 2536-2547.
Pham, X.H., et al., "Electrochemical Characterization of a Single-Walled Carbon Nanotube Electrode for Detection of Glucose," Analytica Chimica Acta, (2010), vol. 671, pp. 36-40.
Pilolli, R., et al., "Advances in biosensor development based on integrating nanotechnology and applied to food-allergen management," Trends in Analytical Chemistry, Jun. 1, 2013, v. 47, pp. 12-26.
Plata, D.L., et al., "Thermogravimetry-Mass Spectrometry for Carbon Nanotube Detection in Complex Mixtures," American Chemical Society Environ. Sci. Technol., (2012), vol. 46, pp. 12254-12261.
Pumera, M., et al., Graphene for electrochemical sensing and biosensing. TrAC Trends in Analytical Chemistry, Oct. 2010, vol. 29, Issue 9, pp. 954-965.
Pumera, M., Graphene in biosensing. materialstoday, Jul.-Aug. 2011;14(7-8):308-315.
Qian, Z., et al., "245 Mhz Graphene-Aluminum Nitride Nano Plate Resonator," Transducers 2013, Barcelona, Spain, (Jun. 16-20, 2013), pp. 2005-2008.
Qian, Z., et al., "Single Transistor Oscillator Based on a Graphene-Aluminum Nitride Nano Plate Resonator," (2013) Joint UFFC, EFTF and PFM Symposium, pp. 559-561.
Qian, Z., et al., High Resolution Calorimetric Sensing Based on Aluminum Nitride MEMS Resonant Thermal Detectors, (2014) IEEE, pp. 1-4.
Qian, Z., et al., "1.27 Ghz Graphene-Aluminum Nitride Nano Plate Resonant Infrared Detector," Transducers (2015), Anchorage, Alaska, pp. 1429-1432.
Qian, Z., et al., Graphene as a Massless Electrode for Ultrahigh-Frequency Piezoelectric Nanoelectromechanical Systems, American Chemical Society Nano Lett. (2015), vol. 15, pp. 4599-4604.
Rajabzade, H., et al., Functionalized Carbon Nanotubes With Gold Nanoparticles to Fabricate a Sensor for Hydrogen Peroxide Determination, E-Journal of Chemistry (2012), vol. 9, No. 4, pp. 2540-2549.
Remaggi, F., et al., "Carbon Nanotube Sensor for Vibrating Molecules," New Journal of Physics vol. 15, (2013) Aug. 30, 2016 pp. 1-20.
Resczenski, J., et al., Presentation "Functionalizing Carbon Nanotubes with Antibodies for the Detection of Prostate Cancer Biomarkers," Johnson Group, Sunfest, (2011), pp. 1-14.
Rotariu, L., et al., "Low Potential Thiocholine Oxidation at Carbon Nanotube-Ionic Liquid Gel Sensor," Sensors and Actuators B 150, (2010) pp. 73-79.
Santavicca, D.F., et al., "Bolometric and Nonbolometric Radio Frequency Detection in a Metallic Single-Walled Carbon Nanotube," Applied Physics Letters, (2011), vol. 98, pp. 1-4.
Shampine, L.F., et al., "Solving Index 1 DAES in Matlab and Simulink," Draft Paper Feb. 22, 1999, pp. 1-15.
Sharma, D., et al., Insight into the biosensing of graphene oxide: Present and future prospects. Arabian Journal of Chemistry, Mar. 2016;9(2):238-261.
Sirdeshmukh, R., et al., "Functionalization of Carbon Nanotubes with Antibodies for Breast Cancer Detection Applications," Pro-

(56) References Cited

OTHER PUBLICATIONS ceedings of the 2004 International Conference on MEMS, NANO and Smart Systems, (2004), IEEE pp. 1-6.
Song, Y., et al., "Carbon Nanotube Volatile Organic Liquid Sensor," Applied Physics Letters 95, (2009), pp. 1-4.
Sousa, C., et al., "Sensitive Detection of Cereal Fractions That Are Toxic to Coeliac Disease Patients, Using Monoclonal Antibodies to a Main Immunogenic Gluten Peptide," Celiac Disease—From Pathophysiology to Advanced Therapies, Department of Microbiology and Parasitology, Faculty of Pharmacy, University of Seville, Seville, Spain, (2008).
Stefansson, S., et al., "Targeting Antibodies to Carbon Nanotube Field Effect Transistors by Pyrene Hydrazide Modification of Heavy Chain Carbohydrates," Journal of Nanotechnology vol. 2012, Article ID 490175, pp. 1-8.
Takeda, S., et al., "Application of Carbon Nanotubes for Detecting Anti-Hemagglutinins Based on Antigen—Antibody Interaction," Biosensors and Bioelectronics, vol. 21 (2005) pp. 201-205.
Tooski, S.B., Functionalized Single Wall Carbon Nanotube Sensor in a Perturbed Microwave Resonant Cavity Based Toxin/Pollutant Gas Pressure Sensor, Journal of Applied Physics, vol. 107, (2010), pp. 1-10.
Tooski, S.B., Sense Toxins/Sewage Gases by Chemically and Biologically Functionalized Single-Walled Carbon Nanotube Sensor Based Microwave Resonator, Journal of Applied Physics, vol. 107, (2010), pp. 1-9.
Tooski, SB, et al., "Optical Properties of Carbon Nanotube Gas Sensor," Journal of Applied Physics, vol. 110, (2011), pp. 1-8.
Varghese, et al. "Recent advances in graphene based gas sensors" Sensors and Actuators; 2015; vol. B 218; pp. 160-183.
Vasilescu, Alina, Alis Vezeanu, and Mihaela Badea. "Electrochemical Impedance Spectroscopy Investigations Focused on Food Allergens." Sensing in Electroanalysis. University Press Centre Pardubice, Czech Republic 59-83.
Venturelli E., et al., "Antibody Covalent Immobilization on Carbon Nanotubes and Assessment of Antigen Binding," Small (2011), vol. 7, No. 15, pp. 2179-2187.
Villamizar, R., et al., "Rapid Detection of Aspergillus Flavus in Rice Using Biofunctionalized Carbon Nanotube Field Effect Transistors," Anal Bioanal Chem, (2011), vol. 399 pp. 119-126.
Vlandas, A., et al., "Enzyme-Free Sugar Sensing in Microfluidic Channels With an Affinity-Based Single-Wall Carbon Nanotube Sensor," Analytical Chemistry, vol. 82, No. 14, (Jul. 15, 2010), pp. 6090-6097.
Volkov, A.N., et al., "Effect of Bending Buckling of Carbon Nanotubes on Thermal Conductivity of Carbon Nanotube Materials," Journal of Applied Physics, vol. 111, (2012) pp. 1-12.
Wang, X., et al., "Transparent, Stretchable, Carbon-Nanotube-Inlaid Conductors Enabled by Standard Replication Technology for Capacitive Pressure, Strain and Touch Sensors†," J. Mater. Chem. A, (2013), vol. 1, pp. 3580-3586.
Wardani, N.I., et al., "Zinc Layered Hydroxide-2(3-Chlorophenoxy) Propionate Modified Multi-Walled Carbon Nanotubes Paste Electrode for the Determination of Nano-Molar Levels Copper (II)," Sensors and Actuators B 198, (2014), pp. 243-248.
Wieser H, "Chemistry of Gluten Proteins," Food Microbiology vol. 24, (2007), pp. 115-119.
Xiao, Y., et al., "Anti-HER2 IgY Antibody-Functionalized Single-Walled Carbon Nanotubes for Detection and Selective Destruction of Breast Cancer Cells," BMC Cancer, 2009, vol. 9 No. 351 pp. 1-11.
Xu, J., et al., "Fabrication of a Magnet-Assisted Alignment Device for the Amperometric Detection of Capillary Electrophoresis Using a Carbon Nanotube/Polypropylene Composite Electrode," Electrophoresis (2013), vol. 34, pp. 2017-2024.
Yang, K., et al., "Preparation and Functionalization of Graphene Nanocomposites for Biomedical Applications," Nature Protocols vol. 8 No. 12, (2013) pp. 2393-2403.
Yang, L, et al., "Carbon Nanotube-Sensor-Integrated Microfluidic Platform for Real-Time Chemical Concentration Detection," Electrophoresis (2009), vol. 30, pp. 3198-3205.
Yun, Y., et al., "A Nanotube Array Immunosensor for Direct Electrochemical Detection of Antigen-Antibody Binding," Sensors and Actuators B vol. 123 (2007) pp. 177-182.
Zhan, et al. "Graphene Field-Effect Transistor and Its Application for Electronic Sensing" Small; 2014; vol. 10; No. 20; pp. 4042-4065.
Zhao, C., et al., "Formation of Uniform Reduced Graphene Oxide Films on Modified PET Substrates Using Dropasting Method," Particuology vol. 17 (2014) pp. 66-73.
Li, X., et al., Transfer of Large-Area Graphene Films for High-Performance Transparent Conductive Electrodes, NANO Letters, (2009), vol. 9, No. 12, pp. 4359-4363.
Bonanni, Allessandra et al. "Graphene for Impedimetric Biosensing", Trac Trends in Analytical Chemistry, vol. 37, 2012, pp. 12-21.
Eissa, S., et al., "Electrochemical Immunosensor for the Milk Allergen- Lactoglobulin Based on Electrografting of Organic Film on Graphene Modified Screen-Printed Carbon Electrodes", Biosensors and Bioelectronics, Elsevier Science Ltd. UK, Amsterdam, NL, vol. 38, No. 1, Jun. 6, 2012.
European Search Report for Application No. 19215320, dated Aug. 13, 2020 (9 pages).
Gutes, Albert et al. "Impedimetric Graphene-based Biosensors for the Detection of Polybrominated Diphenyl Ethers", Nanoscale, vol. 5, No. 13, Jan. 1, 2013, pp. 6048.
Interantional Search Report and Written Opinion for Application No. PCT/US2020/027827, dated Aug. 17, 2020 (14 Pages).
International Preliminary Report on Patentability for Application No. PCT/US2019/034043, dated Dec. 3, 2020 (9 pages).
Liu, Yan, and Chris Toumazou. "An ISFEI based sensing array with sensor offset compensation and pH sensitivity enhancement." Proceedings of 2010 IEEE International Symposium on Circuits and Systems. IEEE, 2010.
Nehra et al., "Current trends in nanomaterial embedded field effect transistor-based biosensor." Biosensors and Bioelectronics 74 (2015), pp. 731-743.
Neves, Marta MPS, et al. "Development of Electrochemical Immunosensors for Celiac Disease Clinical Diagnoses and Gluten-Free Food Control", Dec. 21, 2012, https://repositorio-aberto.up.pt/bitstream/102016/80335/2/27705.pdf, pp. 33, 127-130 and 132-133.
Pena-Bahamonde, Janire, et al. "Recent Advances in Graphene-Based Biosensor Technnology with Applications in Life Sciences", J. Nanobiotechnol, Jan. 1, 2018, pp. 75.
Rani, et al., "Operational of ISFET as a pH sensor by using signal modulated reference elctrode." 2009 International Conference on Information and Multimedia Technology . IEEE, 3 pages.
Renaud-Young, Margaret, et al. "Development of an Ultra-Sensitive Electrochemical Sensor for [Delta] 9-tetrahydrocannabinol (THC) and tis metabolites using carbon paper electrodes" Electrochimica Acta, vol. 307, Mar. 21, 2019, pp. 351-359.
Saurabh, S., et al., "Graphene Oxide-Based Biosensor for Food Toxin Detection", Applied Biochemistry and Biotechnology, Humana Press, Inc. New York, vol. 17, No. 3, Jun. 11, 2014.
Yan, et al., "Solution-Gated Graphene Transistors for Chemical and Biological Sensors." Advanced healthcare materials 3.3 (2014), pp. 313-331.

\* cited by examiner

METHODS AND DEVICES FOR DETECTION OF PATHOGENS

CROSS-REFERENCE TO RELATED APPLICATIONS

This application claims the benefit of U.S. Provisional Application No. 62/623,038, entitled "Methods and Devices for Detection for *Listeria monocytogenes* Bacterium," and filed on Jan. 29, 2018. This application also claims the benefit of U.S. Provisional Application No. 62/676,079, entitled "A Graphene Functionalized Sensor," and filed on May 24, 2018. This application also claims the benefit of U.S. Provisional Application No. 62/703,702, entitled "Methods and Devices for Detection of Pathogens," and filed on Jul. 26, 2018. The entire contents of these applications are incorporated by reference herein.

BACKGROUND

The present invention relates generally to methods and devices for the detection of pathogens, such as bacteria and viruses, in a sample, e.g., a food sample.

Pathogens can cause a variety of diseases and can infect subjects through a myriad of modalities, e.g., food supply or contact with an infected individual. By way of example, *Listeria monocytogenes* is a Gram-positive pathogenic bacterium that causes the infection listeriosis. It is a facultative anaerobic bacterium, which is capable of surviving in the presence or absence of oxygen. It is one of the most virulent foodborne pathogens and can lead to fatality, especially in vulnerable populations. Its ability to grow at typical refrigeration temperatures greatly enhances its ability to evade control in human foodstuffs. Conventional methods for detecting *listeria* in food samples can be time-consuming and cumbersome. Similar problems are presented in detection of other pathogens, such as *chlamydia* and gonorrhea.

*Chlamydia* is a genus of pathogenic bacteria that are obligate intracellular parasites. For example, *Chlamydia trachomatis* (*C. trachomatis*) is responsible for causing blindness of millions of infected patients worldwide. Gonorrhea is a sexually transmitted infection (STI) caused by the bacterium *Neisseria gonorrhoeae*. Other pathogenic agents, such as viruses, can also cause a variety of diseases. For example, human papillomavirus infection is an infection caused by human papillomavirus (HPV). In some patients, an HPV infection can result in warts or precancerous lesions.

Accordingly, there is a need for improved methods and systems for detecting pathogenic agents.

SUMMARY

In one aspect, a method of detecting a pathogen, e.g., *listeria* bacterium, *chlamydia* bacteria, gonorrhea bacteria and/or HPV, in a sample is disclosed, which comprises bringing a sample into contact with a graphene layer functionalized with an antibody exhibiting specific binding affinity to the pathogen, monitoring electrical resistance of said antibody-functionalized graphene layer in response to interaction with said sample, and detecting presence of the pathogen in said sample by detecting a change in said electrical resistance indicative of interaction of the pathogen with said antibody-functionalized graphene layer. By way of example, a change in the electrical resistance of the antibody-functionalized graphene layer that exceeds a predefined threshold can indicate the presence of a pathogen of interest in a sample under study. For example, a decrease of the electrical resistance of the graphene layer can indicate the presence of the pathogen in the sample under study. In some embodiments, a temporal pattern of change in the resistance of the underlying antibody-functionalized graphene layer in response to its exposure to a sample under study can be correlated with the presence of a particular pathogen in the sample under study. By way of example, in some such embodiments, the detected temporal pattern of change in the resistance of the underlying antibody-functionalized graphene layer can be compared with a calibration pattern to determine whether a pathogen of interest is present in the sample under study.

In some embodiments, a method according to the present teachings is capable of detecting pathogens, such as *listeria* bacteria, *chlamydia* bacteria, gonorrhea bacteria and HPV in a sample at a concentration as low as 4 cfu (colony forming units) per 100 grams of a sample.

In some embodiments, the graphene layer is incorporated in a device that comprises a substrate, e.g., a glass or a semiconductor substrate, on which the graphene layer is disposed. A pair of electrically conductive pads can be in electrical contact with the graphene layer to facilitate the measurement of the electrical resistance of the graphene layer in response to interaction with a sample under study. In some embodiments, such a device can include a microfluidic structure that is coupled to said semiconductor substrate, where the microfluidic structure has at least one reservoir and a fluidic channel fluidly coupled to the reservoir. The fluid channel can be in fluid communication with at least a portion of the graphene layer, and the reservoir can be configured for receiving a sample.

In a related aspect, a sensor for detecting a pathogen in a sample is disclosed, which comprises a substrate, a graphene layer deposited on a surface of the substrate, where the graphene layer is functionalized with a plurality of antibodies exhibiting specific binding affinity to the pathogen. A reference electrode is disposed in proximity of the antibody-functionalized graphene layer. The sensor can further comprise a microfluidic delivery device coupled to the functionalized graphene layer for delivery of a fluid sample thereto. In some embodiments, the microfluidic device can comprise two fluid reservoirs and a fluid channel connecting said two reservoirs. An AC voltage source can be utilized to apply an AC voltage to the reference electrode to facilitate the detection of a change in at least one electrical property of the antibody-functionalized graphene layer, e.g., its DC resistance, in response to the interaction of the pathogen with that layer. By way of example, the applied AC voltage can have a frequency in a range of about 1 kHz to about 1 MHz and an amplitude in a range of about 1 millivolt to about 3 volts.

In a related aspect, a system for detecting pathogenic agents in a sample is disclosed, which comprises a sensor configured for detecting at least two pathogenic agents. The system comprises a substrate, and a plurality of sensing units disposed on said substrate, where each of said sensing units comprises an antibody-functionalized graphene layer disposed on said substrate. At least two of said sensing units comprise antibodies configured for specific binding to at least two different pathogens.

In some embodiments, the above system includes at least one reference electrode for application of an AC signal to at least one of the sensing units. In some such embodiments, a plurality of reference electrodes are provided, each of which is configured for application of an AC signal to one of the sensing units. By way of example, the AC signal can have a frequency in a range of about 1 kHz to about 1 MHz and an amplitude in a range of about 1 millivolt to about 3 volts.

In some embodiments, the system can further include a device for measuring the resistance of the underlying graphene layer for detecting a change, if any, in the resistance of the underlying graphene layer in response to its exposure to a sample under investigation. By way of example, the system can include at least one voltage measuring device for measuring a voltage developed across one or more of said sensing units in response to application of a predefined current thereto. An analyzer in communication with the voltage measuring device can receive the measured voltage and utilize the measured voltage together with the predefined current applied to a sensing unit to determine the resistance of the graphene layer associated with that sensing unit. The analyzer can further determine whether the calculated resistance of the sensing unit is indicative of the presence of a pathogen of interest in a sample that was brought into contact with the sensing unit, for example, in a manner discussed above.

In some embodiments, a multiplexer can be disposed between the voltage measuring device and the sensing units to allow sequential measurement of the voltages developed across the sensing units of the sensor in response to application of a predefined current thereto.

In some embodiments, a sensor according to the present teachings includes a plurality of sensing units, each of which is functionalized with a different antibody exhibiting specific binding affinity to a different pathogen. A microfluidic device is coupled to the sensing units for dividing a sample among the sensing units. The microfluidic device can include an input port for receiving a fluid sample, an input manifold for dividing the sample among a plurality of channels each of which is in communication with one of the sensing units. A return manifold can receive the fluid exiting the sensing units and can return the fluid to the input manifold to provide a closed-loop circulation path. In some cases, rather than utilizing a single return path, each sensing unit can include its dedicated fluid return path. In some embodiments, one or more pumps can be employed to facilitate the circulation of the sample through the microfluidic channels.

Further understanding of various aspects of the invention can be obtained by reference to the following detailed description in conjunction with the associated drawings, which are briefly described below.

DETAILED DESCRIPTION

Figure 1A:
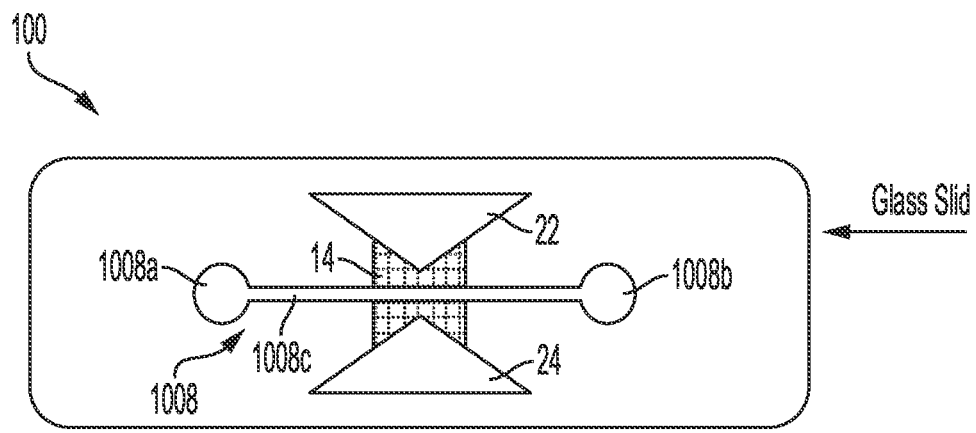
FIG. 1A is a schematic top view of a sensor system according to an embodiment of the present teachings for detecting a pathogen in a sample.

It has been discovered that an anti-body functionalized graphene layer can be employed to detect the presence of pathogenic agents, such as *Listeria monocytogene* bacterium (herein referred to as "*listeria*") in a sample, for example, a food sample, a biological sample, such as urine and saliva. In particular, the interaction of a pathogen in a sample under investigation with the antibody-functionalized graphene layer can cause a change in at least one electrical property of the underlying graphene layer, e.g., a change in the electrical resistance of the underlying graphene layer. A detection of such a change in the electrical property of the underlying graphene layer can be employed to detect the presence of the pathogen in the sample under study. In some embodiments, the detection of a pathogen via an antibody-functionalized graphene layer can be facilitated via application of an AC signal to a reference electrode disposed in proximity of the graphene layer, e.g., positioned at a distance in a range of about 50 microns to about a few millimeter (e.g., 1-2 mm) from the graphene layer. By way of example, the frequency of the AC signal applied to the reference electrode can be in a range of about 1 kHz to about 1 MHz and the amplitude of the AC signal can be in a range of about 1 millivolt to about 3 volts.

Various terms are used herein in accordance with their ordinary meanings in the art. The term "about" as used herein to modify a numerical value is intended to denote a variation of at most 10% of the numerical value.

An "antibody", as that term is used herein, refers to a polypeptide exhibiting specific binding affinity, e.g., an immunoglobulin chain or fragment thereof, comprising at least one functional immunoglobulin variable domain sequence. An antibody encompasses full length antibodies and antibody fragments. In some embodiments, an antibody comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes. In embodiments, an antibody refers to an immunologically active, antigen-binding portion of an immunoglobulin molecule, such as an antibody fragment.

An antibody fragment, e.g., functional fragment, comprises a portion of an antibody, e.g., Fab, Fab', F(ab')2, F(ab)2, variable fragment (Fv), domain antibody (dAb), or single chain variable fragment (scFv). A functional antibody fragment binds to the same antigen as that recognized by the intact (e.g., full-length) antibody.

The term "antibody" also encompasses whole or antigen binding fragments of domain, or single domain, antibodies, which can also be referred to as "sdAb" or "VHH." Domain antibodies comprise either $V_H$ or $V_L$ that can act as stand-alone, antibody fragments. Additionally, domain antibodies include heavy-chain-only antibodies (HCAbs). Antibody molecules can be monospecific (e.g., monovalent or bivalent), bispecific (e.g., bivalent, trivalent, tetravalent, pentavalent, or hexavalent), trispecific (e.g., trivalent, tetravalent, pentavalent, hexavalent), or with higher orders of specificity (e.g, tetraspecific) and/or higher orders of valency beyond hexavalency. An antibody molecule can comprise a functional fragment of a light chain variable region and a functional fragment of a heavy chain variable region, or heavy and light chains may be fused together into a single polypeptide.

In many embodiments, an antibody is a glycoprotein produced by B lymphocytes in response to stimulation with an immunogen. An antibody can be composed of 4 polypeptides—2 heavy chains and 2 light chains—bound together by disulfide bonds to form a Y-shaped molecule.

Figure 1B:
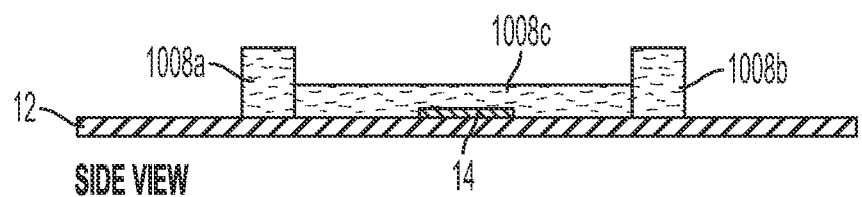
FIG. 1B is a schematic cross-sectional view of the system depicted in FIG. 1A.

FIGS. 1A and 1B schematically depict an example of a device 100 according to an embodiment of the present teachings for detecting a pathogenic agent in a sample. The device 100 includes a substrate 12 on a top surface of which a layer of graphene 14 is deposited. A variety of different substrates can be employed. By way of example, the substrate 12 can be any of a semiconductor, such as silicon, or glass or plastic. In some embodiments in which the substrate 12 is formed of silicon, a layer of silicon oxide can separate the upper graphene layer from the underlying silicon layer.

Figure 2:
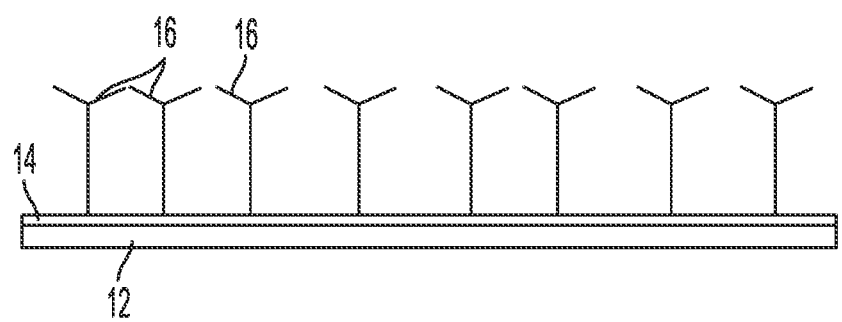
FIG. 2 is a schematic depiction of an antibody-functionalized graphene layer employed in a device according to the present teachings, FIG. 3 schematically depicts a sensor according to an embodiment for detecting pathogens in a sample, where the sensor includes a reference electrode to which an AC voltage can be applied, FIG. 4A schematically depicts a functionalized graphene layer in which a plurality of linker molecules are employed for coupling antibodies to the graphene layer, FIG. 4B schematically depicts the use of a passivation layer to cover the portions of the graphene layer that are not coupled to an antibody molecule.

As shown schematically in FIG. 2, in this embodiment, the graphene layer 14 is functionalized with an antibody 16 that can specifically bind to a pathogen of interest. By way of example, in some embodiments, the graphene layer can be functionalized with *Listeria monocytogenes* antibody LZF7 (BGN/0884/67), which is an IgG2a mouse anti-*Listeria monocytogenes* monoclonal antibody. In another embodiment, the graphene layer can be functionalized with an anti-*chlamydia* antibody, such as monoclonal or polyclonal antibodies. A number of anti-*chlamydia* antibodies are commercially available. For example, anti-*chlamydia* antibody marketed by Genetex under Cat #GTX40387 can be employed. In another embodiment, the graphene layer can be functionalized with anti-gonorrhea antibodies, e.g., monoclonal or polyclonal antibodies. For example, anti-gonorrhea antibody marketed by Creative Diagnostics under Cat #DMZB9759 can be employed. Yet, in another embodiment, the graphene layer can be functionalized with anti-HPV (human papilloma virus) antibodies. For example, anti-HPV antibody marketed by Abcam under Cat #ab2417 or by Thermo Fisher under Cat #MA512446 can be employed.

Figure 4A:
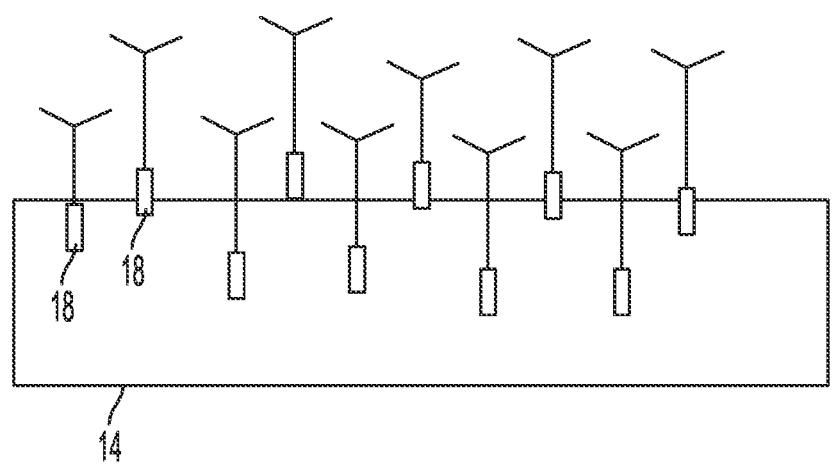

With reference to FIG. 4A, in some embodiments, the antibodies 16 are coupled to the underlying graphene layer via a linker 18, where the linker is covalently attached at one end thereof to the graphene layer. The antibodies can be attached to the other end of the linker, e.g., via a covalent bond. By way of example, in some embodiments, 1-pyrenebutonic acid succinimidyl ester can be employed as the linker to facilitate the coupling of the antibody molecules to the underlying graphene layer. It has been discovered that 1-pyrenebutonic acid succininmidyl ester can be used to couple a variety of different antibodies to the underlying graphene layer. As such, this linker can be used for coupling antibodies that specifically bind to a variety of different pathogens to the underlying graphene layer, where the pathogen-antibody interaction can mediate a change in one or more electrical properties of the underlying graphene layer.

In some embodiments, the graphene layer can be incubated with the linker molecule (e.g., a 5 mM solution of 1-pyrenebutonic acid succimidyl ester) for a few hours (e.g., 2 hours) at room temperature to ensure covalently coupling of the linker molecules to the underlying graphene layer. The linker modified graphene layer can then be incubated with an antibody of interest in a buffer solution (e.g., $NaCO_3$—$NaHCO_3$ buffer solution (pH 9)) at a selected temperature and for a selected duration (e.g., 7-10 hours at 4° C.), followed by rinsing with deionized (DI) water and phosphate buffered solution (PBS). In order to quench the unreacted succinimidyl ester groups, the modified graphene layer can be incubated with ethanolamine (e.g., 0.1 M solution at a pH of 9 for 1 hour).

Figure 4B:
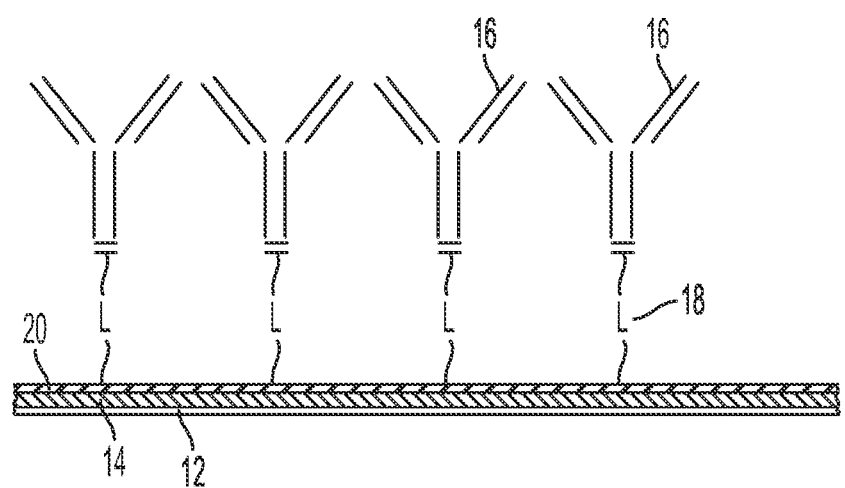

Subsequently, the non-functionalized areas of the graphene layer can be passivated via a passivation layer 20, as shown in FIG. 4B. By way of example, the passivation of the non-functionalized portions of the graphene layer can be achieved, e.g., via incubation with 0.1% Tween 20 or BLOTTO, gelatin and/or amino-PEGS-alcohol (pH 7.4). Further details regarding the use of linkers for attaching antibody molecules to a graphene layer and passivating the non-functionalized portions of the graphene layer can be found, e.g., in U.S. Pat. No. 9,664,674 B2, which is herein incorporated by reference in its entirety.

Referring again to FIGS. 1A and 1B, two metallic pads 22/24 in electrical contact with the graphene layer 14 allow measuring the electrical resistance of the graphene layer, and particularly, a change in the electrical resistance of the graphene layer in response to exposure thereof to a sample containing a pathogen, e.g., *listeria, chlamydia*, gonorrhea bacteria and/or HPV. In some embodiments, the electrically conductive pads can be formed of silver high conductive paste, though other electrically conductive materials can also be employed. The conductive pads can be electrically connected to a measurement device, e.g., a voltmeter, via a plurality of conductive wires for measuring the Ohmic electrical resistance of the graphene layer.

The device 100 further includes a microfluidic structure 1008 having two reservoirs 1008a/1008b and a fluid channel 1008c that fluidly connects the two reservoirs. As shown more clearly in FIG. 1B, the fluid channel can be arranged such that a portion thereof is in fluid contact with a portion of the graphene layer 14.

In some embodiments, in use, a sample suspected of containing a pathogen of interest, e.g., *listeria* bacteria, can be introduced into one of the reservoirs 1008a/1008b and can be made to flow, e.g., via application of hydrodynamic pressure thereto, to the other reservoir through the microfluidic channel 1008c. In this embodiment, a pump (such as pump 3010 depicted in the embodiment of FIG. 3) can be coupled to reservoir 1008b to facilitate the flow of the sample to the other reservoir. In other embodiments, the pump may be coupled to the other reservoir and/or to a fluid channel connecting those reservoirs. The passage of the sample through the channel 1008c brings the pathogen, if any, present in the sample into contact with the antibody-functionalized graphene layer 14. Without being limited to any particular theory, the interaction of the pathogen, e.g., *listeria* bacteria with the antibodies to which they can bind can mediate a change in the electrical conductivity (and hence resistance) of the underlying graphene layer 14, e.g., via charge transfer or other mechanisms. This change in the electrical conductivity of the graphene layer 14 can in turn be measured to detect the presence of the pathogen in the sample under study.

In some embodiments, a four-point measurement technique can be used to measure the resistance of the antibody-functionalized graphene layer in response to exposure thereof to a sample under investigation.

Figure 5:
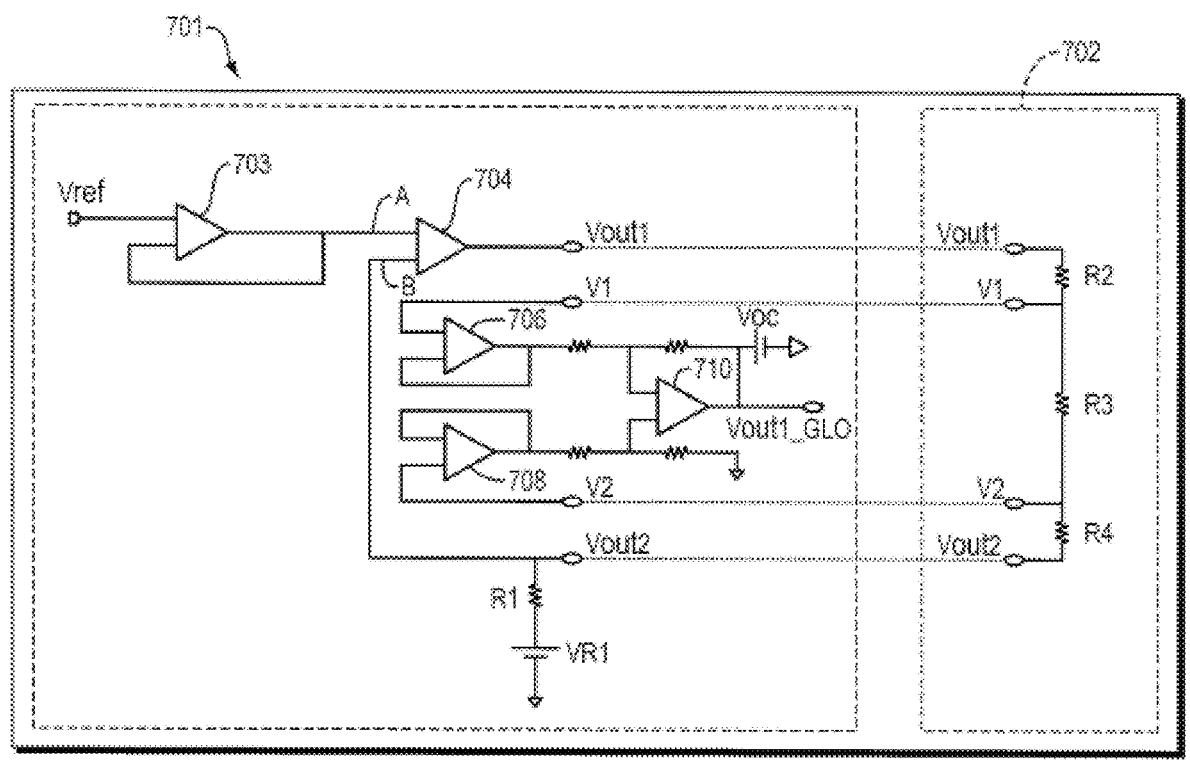
FIG. 5 depicts a circuit diagram of an example of a voltage-measuring device that can be employed for measuring a voltage induced across an antibody-functionalized graphene layer in response to application of a current thereto, FIG. 6A schematically depicts an analyzer in communication with the voltage-measuring device shown in FIG. 5 for receiving the voltage measured by the voltage-measuring device as well as the current applied to the antibody-functionalized graphene layer.

By way of example, FIG. 5 schematically depicts a voltage measuring circuitry 701 that can be employed in some embodiments of the present teachings. This figures shows a sensor 702 as an equivalent circuit corresponding to an antibody-functionalized graphene layer. A fixed voltage V (e.g., 1.2 V) is generated at the output of a buffer operational amplifier 703. This voltage is applied to one input (A) of a downstream operational amplifier 704 whose other input B is coupled to VR1 ground via a resistor R1. The output of the operational amplifier 704 ($V_{out1}$) is coupled to one end of the sensor 702 and the end of the resistor R1 that is not connected to VR1 ground is coupled to the other end of the sensor 702 (in this schematic diagram, resistor R2 denotes the resistance between two electrode pads at one end of the equivalent sensor 702, resistor R3 denotes the resistance of the graphene layer extending between two inner electrodes of the sensor, and resistor R4 denotes the resistance between two electrode pads at the other end of the sensor). As the operational amplifier maintains the voltage at the end of the resistor R1 that is not connected to VR1 ground at the fixed voltage applied to its input (A), e.g., 1.2 V, a constant current source is generated that provides a constant current flow through the sensor 702 and returns to ground via the resistor R1 and VR1.

The voltage generated across the antibody-functionalized graphene layer is measured via the two inner electrodes of the sensor. Specifically, one pair of the inner electrode pads is coupled to a buffer operational amplifier 706 and the other pair is coupled to the other buffer operational amplifier 708. The outputs of the buffer operational amplifiers are applied to the input ports of a differential amplifier 710 whose output port provides the voltage difference across the antibody-functionalized graphene layer. This voltage difference ($V_{out1}$–GLO) can then be used to measure the resistance exhibited by the antibody-functionalized graphene layer. The current forced through R3 is set by I=(Vref–VR1)/R1, where the value of VR1 is digitally controlled. For each value of current I, the corresponding voltage (Vout1_GLO) is measured and stored. The resistance of the antibody-functionalized graphene layer can be calculated as the derivative of the voltage, Vout1_GLO, with respect to current I, i.e., R=dV/dI.

Figure 6A:
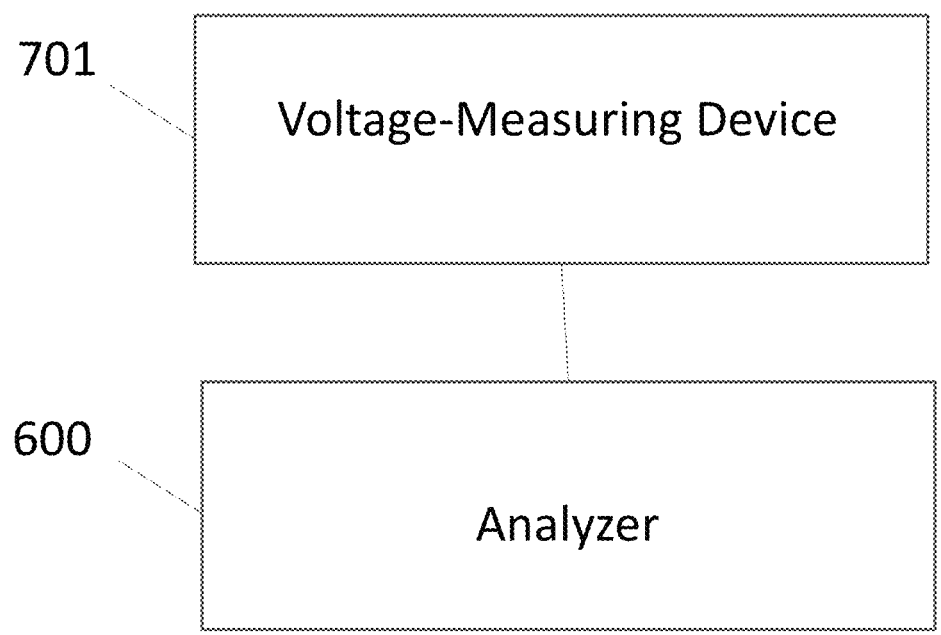
FIG. 6B depicts an example of implementation of the analyzer shown in FIG. 6A, FIG. 7 schematically depicts a sensor according to an embodiment, which includes a plurality of sensing units configured to detect different types of pathogens, FIG. 8 schematically depicts a microfluidic device that is coupled to the sensor shown in FIG. 7 for delivering a liquid sample thereto, FIG. 9 schematically depicts a sensor according to an embodiment of the present teachings, which includes a plurality of sensing unit having graphene layers functionalized with different antibodies and a microfluidic device for introducing a sample onto the sensing units.

As shown schematically in FIG. 6A, in some embodiments, an analyzer 600 can be in communication with the voltage measuring circuitry 701 to receive the applied current and the measured voltage value and use these values to calculate the resistance of the antibody-functionalized graphene layer. The analyzer can then employ the calculated resistance, e.g., a change in the resistance in response to exposure of the antibody-functionalized graphene layer to a sample under investigation, to determine, in accordance with the present teachings, whether the sample contains a pathogen of interest.

Figure 6B:
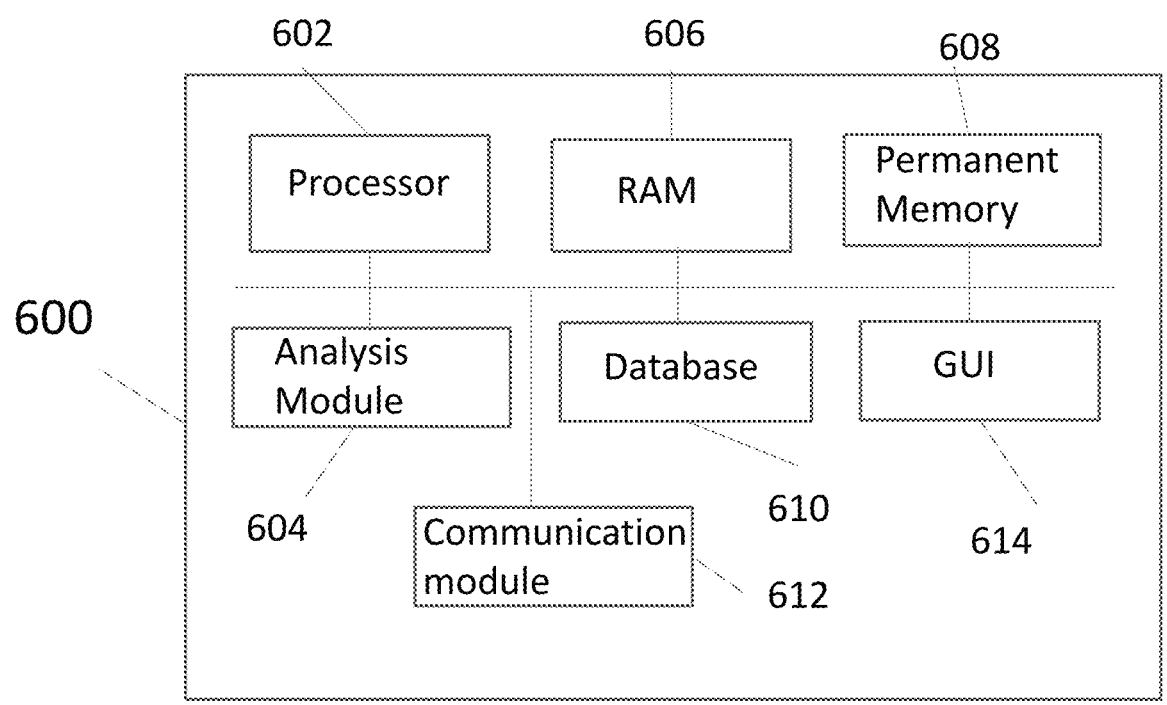

By way of example, as shown schematically in FIG. 6B, in this embodiment, the analyzer 600 can include a processor 602, an analysis module 604, a random access memory (RAM) 606, a permanent memory 608, a database 610, a communication module 612, and a graphical user interface (GUI) 614. The analyzer 600 can employ the communication module 612 to communicate with the voltage measuring circuitry 701 to receive the values of the applied current and the measured voltage. The communication module 612 can be a wired or a wireless communication module. The analyzer 600 further includes a graphical user interface (GUI) 614 that allows a user to interact with the analyzer 600.

The analysis module 604 can employ the values of a current applied to the antibody-functionalized graphene layer as well as the voltage induced across the graphene layer to calculate a change in the resistance of the antibody-functionalized graphene layer in response to exposure thereof to a sample under investigation. The instructions for such calculation can be stored in the permanent memory 608 and can be transferred at runtime to RAM 606 via processor 602 for use by the analysis module 604. In some embodiments, the database 610 can store calibration data that can be employed for determining whether a pathogen of interest is present in a sample under study. By way of example, the database 610 can store calibration data indicative of a temporal change in the electrical resistance of an antibody-functionalized graphene layer in response to exposure to a particular pathogen. A comparison of a measured temporal variation of a similar antibody-functionalized graphene exposed to a sample suspected of containing the pathogen with the calibrated response can be used to determine whether the pathogen is present in the sample. The GUI 614 can allow a user to interact with the analyzer 600.

Figure 3:
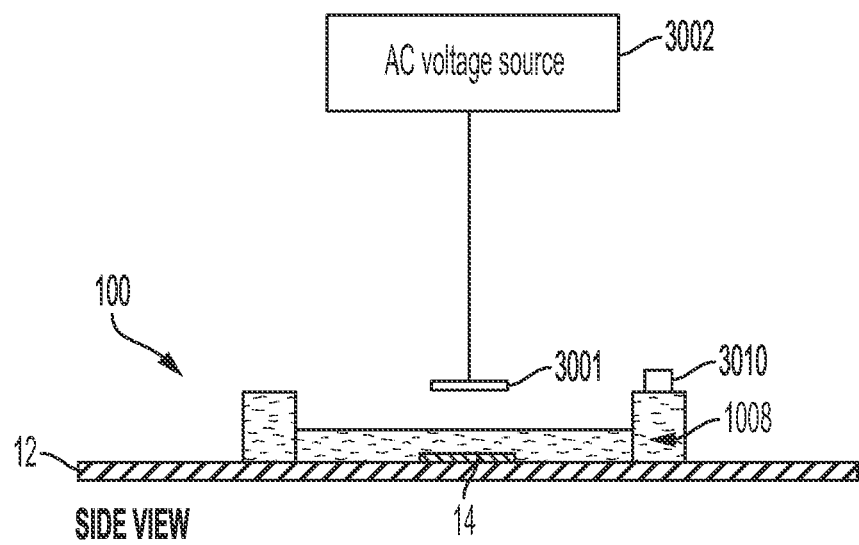

Referring to FIG. 3, in some embodiments, the sensor 100 according to an embodiment can include a reference electrode 3001 disposed in proximity of the antibody-functionalized graphene layer 14, e.g., at a distance in a range of about 50 micrometers to about a few millimeters (e.g., 1-2 millimeters) above the functionalized graphene layer. In some embodiments, the distance of the reference electrode relative to the functionalized graphene layer 14 can be in a range of about 100 microns to about 1 millimeter, or in a range of about 200 microns to about 0.5 millimeter. Further, in some embodiments, rather than being positioned above the graphene layer, the reference electrode can be positioned in the same plane as the graphene layer.

The reference electrode can be utilized to generate a time-varying electric field at the interface of the functionalized graphene layer and a liquid sample, e.g., a liquid sample suspected of containing one or more pathogens, that is brought into contact with that layer. For example, in this embodiment, an AC voltage source 3002 can be employed to apply an AC voltage to the reference electrode, which can in turn result in the generation of a time-varying electric field in the space between the reference electrode and the functionalized graphene layer.

The AC reference electrode 3001 can be formed of any suitable electrical conductor. Some examples of suitable conductors include, without limitation, silver, copper, and gold. In some embodiments, the thickness of the reference electrode 3001 can be, for example, in a range of about 100 nm to about 400 micrometers (microns), e.g., in a range of about 1 microns to about 100 microns, though other thicknesses can also be employed.

The application of such a time-varying electric field via the reference electrode to the interface between the graphene layer 14 and a liquid sample in contact with the graphene layer can advantageously facilitate the detection of one or more electrical properties of the antibody-functionalized graphene layer, e.g., a change in its resistance in response to its interaction with a pathogen present in the sample that exhibits specific binding to the antibody of the functionalized graphene layer. In particular, it has been discovered that the application of an AC voltage having a frequency in a range of about 1 kHz to about 1 MHz, e.g., in a range of about 10 kHz to about 500 kHz, or in a range of about 20 kHz to about 400 kHz, or in a range of about 30 kHz to about 300 kHz, or in a range of about 40 kHz to about 200 kHz, can be especially advantageous in this regard. By way of example, the amplitude of the AC voltage applied to the reference electrode can be in a range of about 1 millivolt to about 3 volts, e.g., in a range of about 100 millivolts to about 2 volts, or in range of about 200 millivolts to about 1 volt, or in range of about 300 millivolts to about 1 volt, e.g., in a range of about 0.5 volts to 1 volt. Further, in some cases, the voltage applied to the reference electrode can have an AC component and a DC offset, where the DC offset can be in a range of about −40 volts to about +40 volts, e.g., −1 volt to about +1 volt.

Without being limited to any particular theory, in some embodiments, it is expected that the application of such a voltage to the reference electrode can minimize, and preferably eliminate, an effective capacitance associated with a sample, e.g., a liquid sample, with which the functionalized graphene layer is brought into contact as the sample is being tested, thereby facilitating the detection of a change in the resistance of the underlying graphene layer in response to the interaction of the antibodies with a respective pathogen. In some cases, the effective capacitance of the sample can be due to ions present in the sample.

The present teachings can be applied to detect a variety of pathogens, such as those discussed above, in a variety of different samples. Some examples of samples that can be interrogated include, without limitation, food samples and bodily fluids, such as blood, urine, saliva, etc.

In some embodiments, a sensor according to the present teachings is capable of detecting pathogens in a variety of different sample types including, without limitation, urine, mucous and/or blood. In some cases, e.g., when the detection of *chlamydia* is desired, the sample can be obtained by a swab, e.g., an endocervical swab. Other methods known in the art for obtaining samples can also be utilized.

Figure 7:
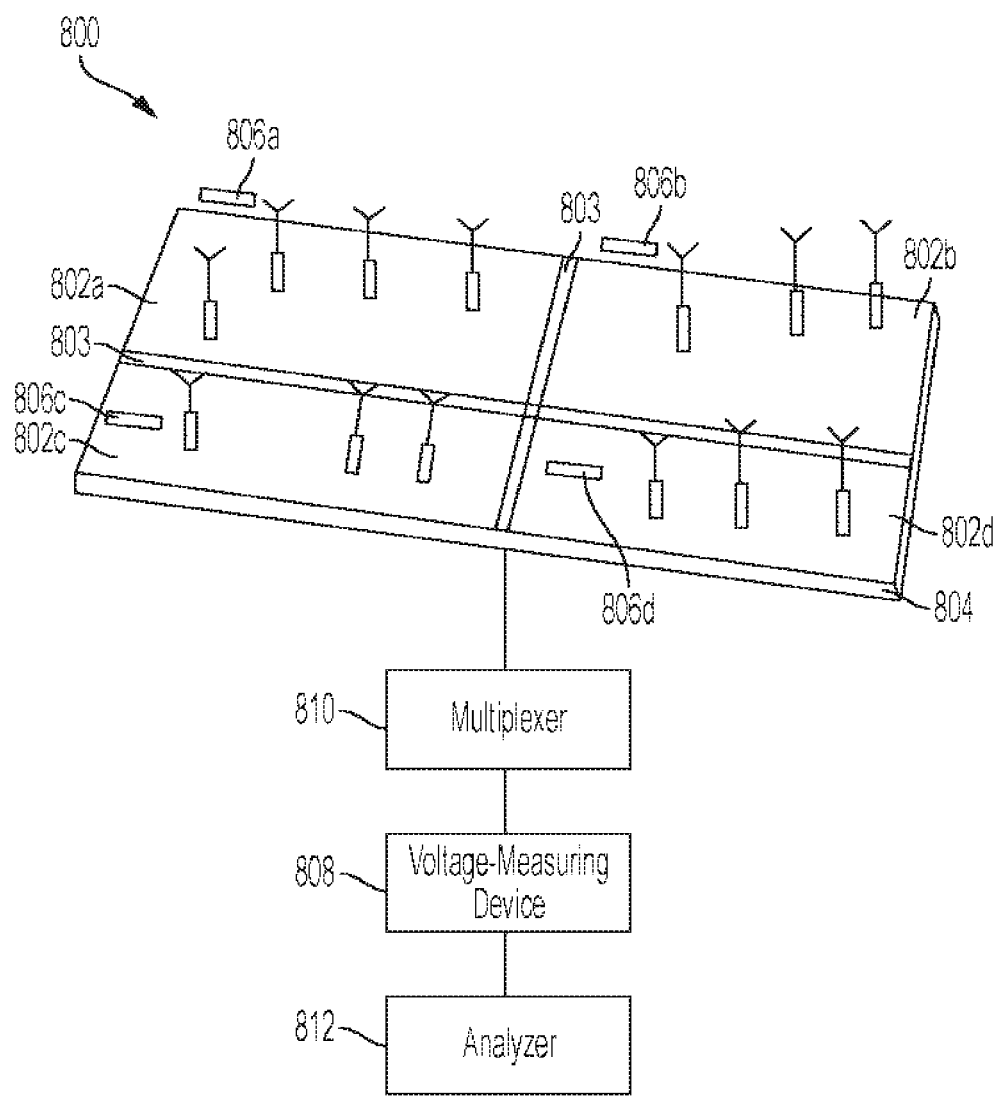

With reference to FIG. 7, in some embodiments, a graphene-based sensor 800 according to the present teachings can include a plurality of sensing units 802a, 802b, 802c, and 802d, (herein collectively referred to as sensing units 802), each of which is configured for the detection of a different pathogen. In this embodiment, the sensing units 802 are formed on a single underlying substrate 804, e.g., a semiconductor (such as silicon), glass or plastic. Each sensing unit includes an antibody-functionalized graphene layer, fabricated in a manner discussed above. In this embodiment, at least two sensing units are functionalized with two different antibodies suitable for the detection of two different pathogens. For example, one sensing unit can be functionalized with an antibody that specifically binds to *listeria* bacterium and another sensing unit can be functionalized with an antibody that specifically binds to *chlamydia* bacterium. In some embodiments, each of the sensing units is functionalized with an antibody suitable for the detection of a different pathogen. By way of example, the number of sensing units can range from 2 to 20, though other numbers can also be employed.

The sensing units 802 are electrically insulated from one another via an electrically insulating network 803. By way of example, the electrically-insulating network 803 can be in the form of a plurality of electrically-insulating strips formed, e.g., of silicon oxide (such as $SiO_2$), which can electrically isolate different sensing units from one another. Further, in this embodiment, each of the sensing units 800 includes a reference electrode 806a, 806b, 806c, and 806d (herein referred to collectively as reference electrodes 806) to which AC signals can be applied, e.g., in a manner discussed above, to facilitate the detection of a pathogen of interest. While in some embodiments, the frequency and amplitude of the AC signal applied to the different sensing units can be the same, in other embodiments, the AC signals applied to at least two different sensing units can exhibit different frequencies and/or amplitudes.

In some embodiments, rather than employing multiple reference electrodes, a single reference electrode can be employed for applying a reference AC voltage to multiple, or all, of the sensing units 802. The frequency and the amplitude of the applied reference AC voltage can be, for example, in the ranges discussed above.

With continued reference to FIG. 7, a voltage measuring device 808 can be employed to measure a voltage across each of the sensing units in response to application of a predefined constant current thereto, e.g., in a manner discussed above in connection with the voltage measuring device 701. In this embodiment, a multiplexer 810 can be employed to selectively measure the voltage induced across the sensing units in response to application of a predefined current thereto, e.g., in a time-wise sequential manner. An analyzer 812, such as the above analyzer 600, can receive the voltage data from the voltage measuring device 808 and can calculate the change in the electrical resistance of the underlying graphene layer to determine whether one or more of the pathogens are present in the sample under study.

Figure 8:
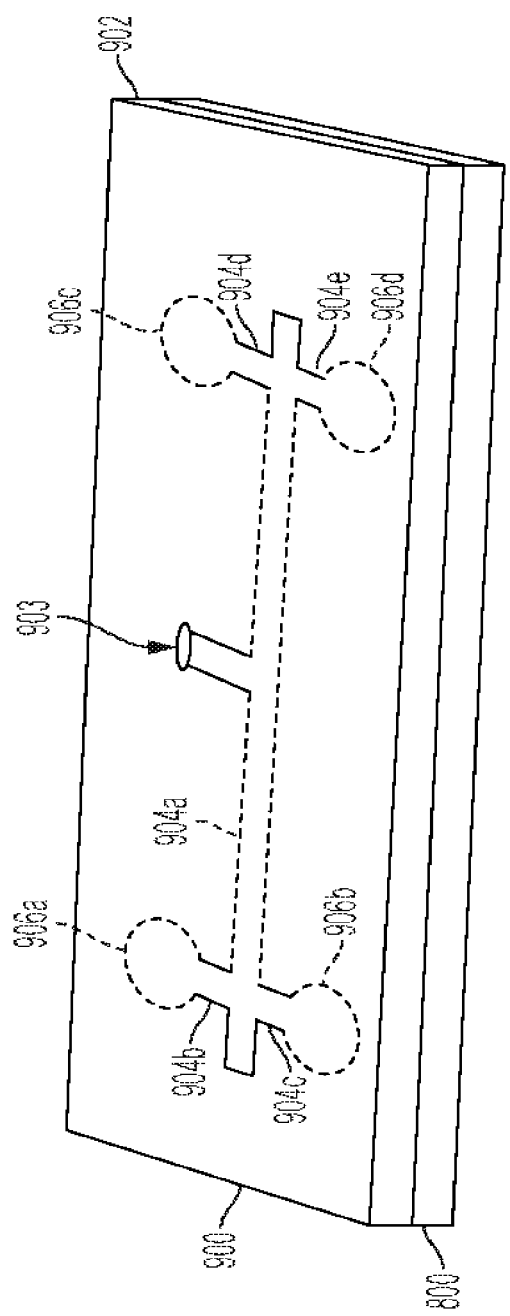

With reference to FIG. 8, in some embodiments, a microfluidic device 900 can be fluidly coupled to the sensor 800 for delivering a liquid sample suspected of containing one or more pathogens of interest to the sensor 800. In this embodiment, the microfluidic device 900 includes a body 902 having an input port 903 for receiving a sample. Each of a plurality of internal channels 904a, 904b, 904c, 904d and 904e (herein collectively referred to as channels 904) in fluid communication with the input port 903 can receive a portion of the sample via the input port 903 and guide those portions to output ports 906a, 906b, 906c, and 906d (herein collectively referred to as output ports 906), which in turn deliver those sample portions to the sensing units for analysis.

Figure 9:
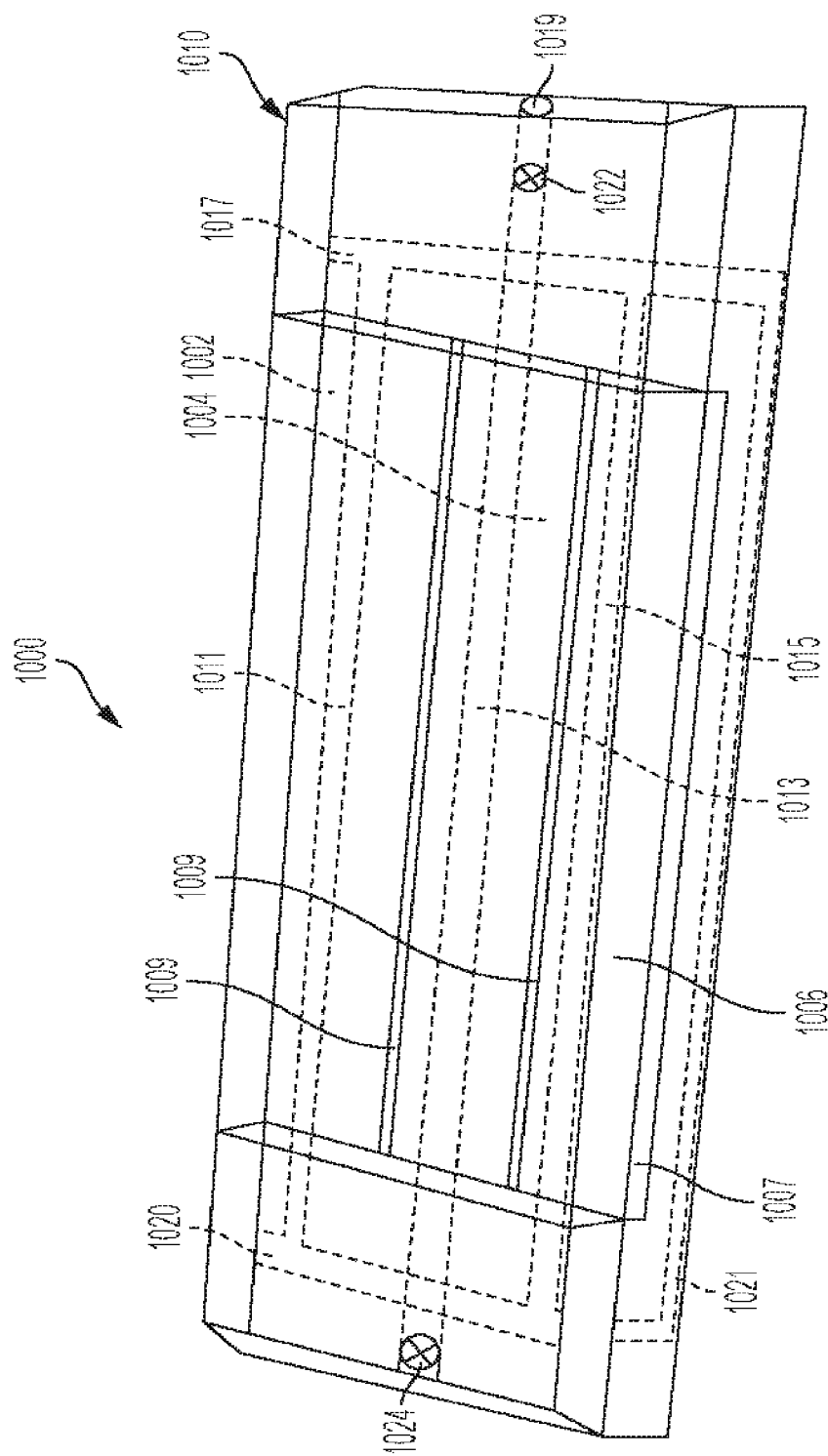

FIG. 9 schematically depicts another embodiment of a sensor 1000 according to the present teachings, which includes sensing units 1002, 1004, and 1006 are disposed. Each of the sensing units 1002, 1004, and 1006 includes a graphene layer that is functionalized with an antibody that exhibits specific binding for a different pathogen, in a manner discussed above. In this embodiment, the graphene layers of the sensing units 1002, 1004, and 1006 are deposited on the top surface of a single underlying substrate 1007, e.g., a silicon substrate. In this embodiment, the sensing units are separated from one another by a plurality of electrically insulating strips 1009, which can be formed, e.g., from silicon oxide.

With continued reference to FIG. 9, in this embodiment, a microfluidic device 1010 is coupled to the sensing units 1002, 1004, and 1006 for delivering a sample under investigation to the sensing units. In this embodiment, the microfluidic device 1010 includes three fluidic channels 1011, 1013, and 1015, e.g., each of which has a diameter in a range of about 10 microns to about 100 microns and is in fluid communication with the antibody-functionalized graphene layer of one of the sensing units. The channels 1011, 1013, and 1015 are fluidically coupled via an input manifold 1017 to an input port 1019 through which a sample can be introduced into the microfluidic device 1010. The input manifold 1017 can distribute a portion of the received sample to each of the channels 1011, 1013 and 1015. The channels 1011, 1013 and 1015 terminate in an return manifold 1020 that is in turn fluidly coupled to a return channel 1021, which can direct the fluid back to the input manifold, thereby providing closed-loop fluid circulation. A input pump 1022, e.g., a gear pump, can facilitate the flow of the sample into the input manifold, and a return pump 1024 can facilitate the return of the fluid exiting the channels 1011, 1013, and 1015 back to the input manifold 1017.

In some embodiments, rather than employing a single return microfluidic channel, a plurality of return microfluidic channels, each associated with one of the sensing units, can be employed.

Similar to the previous embodiment, a change of the electrical resistance of the antibody-functionalized graphene layer of each sensing unit can be measured and correlated with the presence of a particular pathogen for which that sensing unit is configured.

Although in the above embodiments, the resistance of the antibody-functionalized graphene layer is measured via application of a predefined current to the graphene layer following by measuring a voltage induced across the graphene layer, in other embodiments, a predefined voltage can be applied across the graphene layer and a current flow through the graphene layer caused by the applied voltage can be measured. The values of the voltage and current can then be employed, for example, in a manner discussed above, to arrive at the resistance of the graphene layer (e.g., using Ohm's law).

A sensor according to the present teachings can be employed in a variety of settings. By way of example, a sensor according to the present teachings can be employed in a medical setting. Further, a sensor according to the present teachings can be employed for home use. In such cases, the analyzer can be implemented on a mobile device. In addition or alternatively, the analyzer can be implemented on a remote server that can be in communication with the sensor via a network, e.g., the Internet, to receive sensing data, such as a voltage measured across the antibody-functionalized graphene layer. The analyzer can employ the sensing data to determine whether a pathogen of interest is present in a sample under study in a manner discussed above.

The following example is provided for further elucidation of various aspects of the invention and is not intended to provide necessarily the optimal way of practicing the present teachings or optical results that can be obtained.

EXAMPLE

A microfluidic chip based on the design depicted in FIGS. 1A and 1B was fabricated. The conductive pads were formed of Silver high conductive paste purchased from MG Chemicals of Canada. The high conductive paste was employed to electrically connect the graphene layer to a measurement circuit for detecting the electrical response of the graphene layer to a test sample containing heat-killed *Listeria monocytogenes*.

The graphene layer was functionalized with *Listeria monocytogenes* Antibody LZF7 (BGN/0884/67), which is an IgG2a Mouse anti *Listeria monocytogenes* Monoclonal Antibody and was purchased from Bio-Rad. The functionalization process included covalently attaching a plurality of linker molecules to the graphene layer at one end thereof and coupling the antibody molecules to the other end of the linker molecules. In this example, the linker molecule was 1-pyrenebutonic acid succinimidyl ester. The procedures for attaching the linker molecules to the graphene layer and coupling antibody molecules to the linker molecules described in U.S. Pat. No. 9,664,674 B2, which is herein incorporated by reference in its entirety, were followed.

A freeze-dried heat-killed preparation of *Listeria monocytogenes* (HKLM) was purchased from InvivoGen of San Diego, Calif. After mixing the *listeria* preparation with endotoxin-free water, 1 mL of the resultant solution contained $10^7$ to $10^8$ bacteria. The bacteria were then stained by 5% violet crystal solution purchased from Sigma-Aldrich and washed 4 times by deionized (DI) water to remove the excessive dies in the solution. Then, in two steps, the solution was diluted to $10^4$ to $10^3$ bacteria per mL.

Subsequently, 1 mL of the sample was mixed with 9 mL of the Phosphate-buffered saline (PBS) buffer to achieve a concentration of $10^3$ to $10^2$ bacteria per mL. The sample was then injected into the chip by using a syringe pump at the rate of 1 mL/hour for two hours (phase 1). Then the syringe was disconnected and blank PBS buffer solution was pumped in to the chip for another two hours (Phase 2). Then the vial was disconnected and *Listeria* sample again was injected into the chip for another 2 hours.

Figure 10:
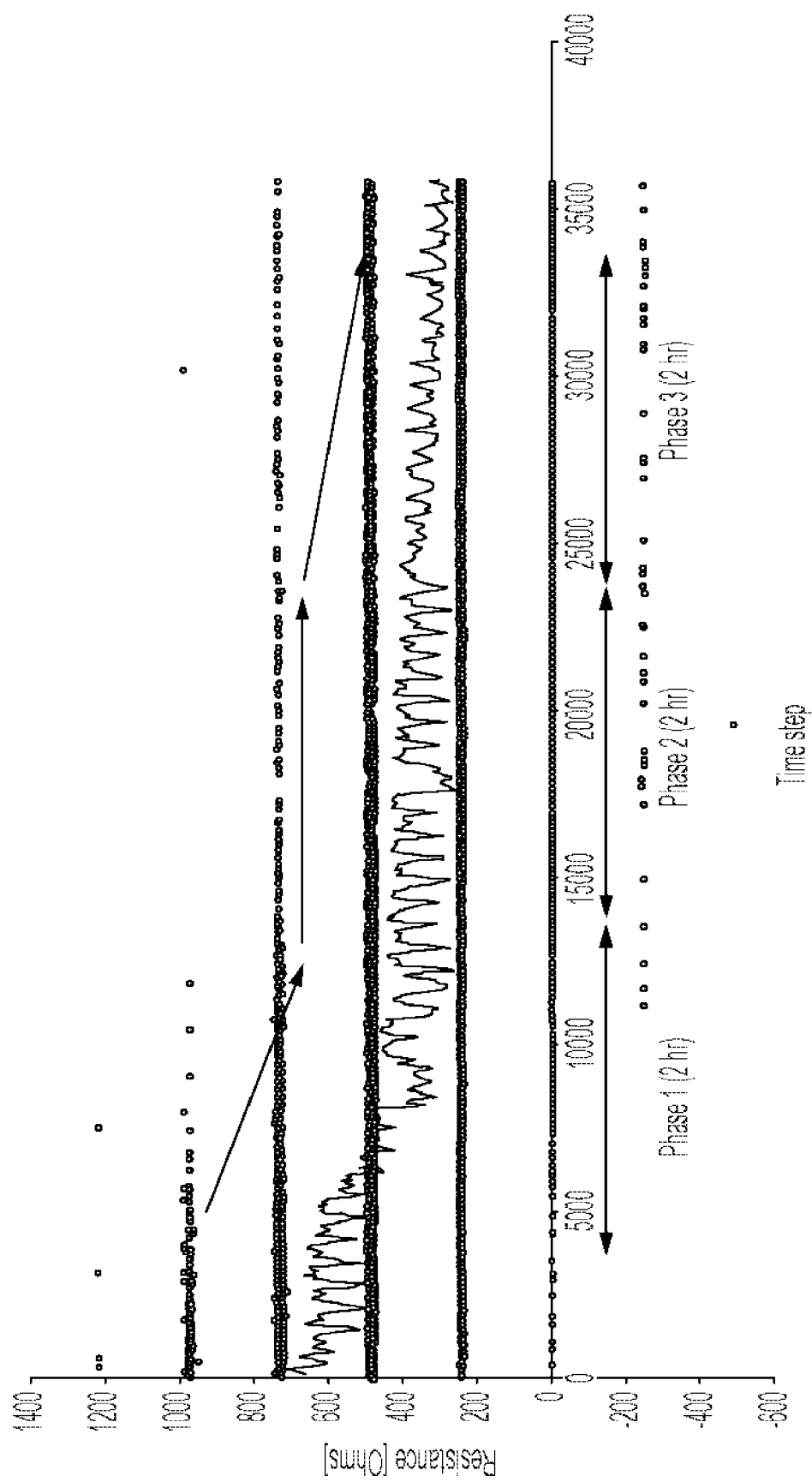
FIG. 10 presents data indicative of detection of *Listeria* using an embodiment of the present teachings.

The electrical resistance of the graphene was monitored using a four-probe based circuit such that the one described in the aforementioned U.S. Pat. No. 9,664,674 and data was recorded on the connected computer. The results are shown in the graph presented in FIG. 10. The data shows that the resistance of the graphene layer decreases during phase 1 as the bacterial cells interact with the antibody-functionalized graphene layer. During phase 2, no change in the resistance of the graphene layer is observed. This shows that the change in the resistance of the graphene layer observed during phase 1 can be attributed to the interaction of the *listeria* bacteria with the antibody-functionalized graphene. As the sample containing bacterial cells is reintroduced into the chip during phase 3, the resistance of the graphene layer begins to decrease again, albeit at a smaller slope relative to the change of resistance observed during phase 1. Without being limited to any particular theory, the smaller slope observed during phase 2 may be due to a lower number of available sites on the antibody-functionalized graphene with which the *listeria* bacteria can interact.

The above data clearly shows that the detection of *listeria* bacteria, even at small concentrations, is feasible by using the present teachings.

Those having ordinary skill in the art will appreciate that various changes can be made to the above embodiments without departing from the scope of the invention.

The invention claimed is:

1. A method of detecting a pathogenic agent in a sample, comprising:
   bringing a sample into contact with a graphene layer of a sensor, wherein said graphene layer is functionalized with an antibody exhibiting specific binding affinity to said pathogenic agent, and wherein said sensor further comprises a plurality of conductive pads in electrical contact with said graphene layer to allow measurement of at least one electrical property of the antibody-functionalized graphene layer in response to interaction thereof with said sample, said sensor further comprising a reference electrode disposed in proximity of said antibody-functionalized graphene layer, applying an AC signal to said reference electrode so as to generate a time-varying electric field extending between said reference electrode and said antibody-functionalized graphene layer, monitoring said at least one electrical property of said antibody-functionalized graphene layer in response to interaction with said sample, and detecting presence of said pathogenic agent in said sample by detecting a change in said at least one electrical property indicative of interaction of said pathogenic agent with said antibody-functionalized graphene layer.

2. The method of claim 1, wherein said time-varying electric field has a frequency in a range of about 1 kHz to about 1 MHz.

3. The method of claim 1, wherein said graphene layer is disposed on an underlying substrate.

4. The method of claim 3, wherein said underlying substrate is any of a semiconductor substrate and a glass substrate.

5. The method of claim 3, wherein a microfluidic structure is coupled to said underlying substrate, said microfluidic structure having at least one reservoir and a fluidic channel fluidly coupled to said at least one reservoir, said fluidic channel being in fluid communication with at least a portion of said graphene layer, and said at least one reservoir being configured for receiving a sample.

6. The method of claim 1, wherein said pathogenic agent comprises *listeria* bacteria.

7. The method of claim 1, wherein said pathogenic agent comprises *chlamydia* bacteria.

8. The method of claim 1, wherein said pathogenic agent comprises gonorrhea bacteria.

9. The method of claim 1, wherein said pathogenic agent comprises HPV.

10. The method of claim 1, wherein said at least one electrical property includes an electrical resistance.

11. The method of claim 1, wherein said time-varying electric field has a frequency in a range of about 10 kHz to about 1 MHz.

12. The method of claim 1, wherein said time-varying electric field has a frequency in a range of about 10 kHz to about 500 KHz.

13. The method of claim 1, wherein said time-varying electric field has a frequency in a range of about 20 kHz to about 400 KHz.

14. The method of claim 1, wherein said time-varying electric field has a frequency in a range of about 30 kHz to about 300 KHz.

15. The method of claim 1, wherein said time-varying electric field has a frequency in a range of about 40 kHz to about 200 KHz.

16. The method of claim 1, wherein said reference electrode is disposed at a distance in a range of about 50 microns to about 2 mm from said antibody-functionalized graphene layer.

17. The method of claim 1, wherein a DC offset is further applied to said reference electrode.

18. The method of claim 1, wherein said at least one electrical property is measured based on a four-point measurement technique using said plurality of conductive pads that are in electrical contact with said graphene layer.

* * * * *